United States Patent [19]
Ott

[11] 3,990,436
[45] Nov. 9, 1976

[54] INDIVIDUAL IDENTIFICATION AND DIAGNOSIS USING WAVE POLARIZATION

[75] Inventor: James H. Ott, Akron, Ohio

[73] Assignee: Novar Electronics Corporation, Barberton, Ohio

[22] Filed: Aug. 25, 1975

[21] Appl. No.: 607,234

[52] U.S. Cl. .............................. 128/2 R; 73/67.2; 128/2 V; 340/149 R; 340/279
[51] Int. Cl.² ........................................ A61B 10/00
[58] Field of Search .................. 128/2 R, 2 V, 2 A; 73/67.2; 340/279

[56] References Cited
UNITED STATES PATENTS

| | | | |
|---|---|---|---|
| 3,477,422 | 11/1969 | Jurist, Jr. et al. | 128/2 R |
| 3,598,111 | 8/1971 | Kahn et al. | 73/67.2 X |
| 3,639,905 | 2/1972 | Yaida et al. | 340/149 |
| 3,653,373 | 4/1972 | Batterman | 128/2 K |
| 3,847,141 | 11/1974 | Hoop | 128/2 V |
| 3,872,443 | 3/1975 | Ott | 340/172.5 |

Primary Examiner—Kyle L. Howell
Attorney, Agent, or Firm—Frank H. Foster

[57] ABSTRACT

A method for the medical diagnosis of human and other bodies and also for use in the automatic machine interrogation of individuals for identifying persons such as those seeking credit or admittance to a security area. Oscillatory wave energy, preferably a sonic signal, is applied with a selected polarization to a first part of a body. The polarization of the wave energy transmitted through a portion of the body is detected at a second part of the body. Data representing the shift in polarization is stored for subsequent comparison to a polarization shift which is subsequently measured by the same steps. Comparison of the data representing the two polarization shifts can be used for quantitative and qualitative medical diagnosis as well as for an automatic machine decision whether the polarization shifts are sufficiently similar that they were derived from the same individual. The use of multiple frequencies permits the derivation of a polarization shift characteristic over a range of frequencies. Apparatus is disclosed comprising a wave generating transducer and a plurality of receiving transducers mounted in side-by-side arcuate arrangement for at least partially surrounding the second body part.

11 Claims, 6 Drawing Figures

INDIVIDUAL IDENTIFICATION AND DIAGNOSIS USING WAVE POLARIZATION

BACKGROUND OF THE INVENTION

The invention relates generally to machine analysis, diagnosis and identification of persons and more particularly relates to the use of metering and computing circuitry for detecting and processing data which represents the polarization shift effected by a portion of a body.

Substantial research and developement is currently being done in interfacing human beings and electronic circuitry. For example, in bioengineering work is being done in the harnessing of electronic technology for diagnosing and treating disease. In the area of electronic computers used for business data processing, systems are being sought for the rapid, accurate and automatic machine identification of persons.

In the medical field, circuits have been disclosed for measuring the electrical impedance of portions of the human body. Such circuits are disclosed for example, in U.S. Pats. Nos. 3,085,566 and 3,340,867.

Still other circuits, such as that shown in U.S. Pat. No. 3,334,622, operate on a sonic radar principle utilizing the receipt of echoes to detect the position of organs and other anatomical features of the human body. Another system disclosed in U.S. Pat. No. 3,653,373 applies a sharp blow to a human tooth and records its subsequent oscillation to provide a graph which can be subjectively analyzed by a medical professional to give an indication of peridontal health.

Computer aided identification of persons provides for rapid and automatic determination of the identity of a person prior to admitting that person to a security area or to giving that person access to sensitive data stored in a computer memory. Similarly, such machine identification may be used in credit transactions. A person seeking credit would not only present his credit card to a clerk but in addition would be subjected to machine interrogation and identification to confirm that this person is actually the one who owns the card being presented and is approved for the extension of credit.

Previous attempts to design a computer identification system have been directed toward such things as voice print identification, finger print identification or automatic signature identification. U.S. Pat. No. 3,639,905 discloses an automatic identification system which measures the electrical resistance of the skin surface and additionally measures both the shadow of the human hand and the pulsations of surface reflections from the fingers of the hand.

I have discovered a method for both the identification of individuals and the diagnosis of the health or disease condition of a portion of a human body.

The use of embodiments of my invention will be helpful in determining, by way of example, the condition of a fractured bone and its healing progression and possibly the condition of arterial disease, tumor growth, bone aging or deterioration. Other uses such as those suggested in my U.S. Pat. No. 3,872,443 also have potential with embodiments of the present invention.

SUMMARY AND OBJECTS OF THE INVENTION

It is an object of the present invention to provide a method capable of distinguishing unique characteristics of different bodies and for displaying these characteristics as an aid in identifying persons and in diagnosing their health.

The invention includes a method for determing a body part characteristic, the method comprising measuring the polarization shift effected by said body part upon wave energy transmitted through the body part. The method may be practiced by utilizing a wave energy transducer for applying the wave energy to a first body part at a selected polarization and a circuit means connected to the wave generating transducer for energizing it. The apparatus further comprises a plurality of receiving transducers mounted in side by side arcuate arrangement for at least partially surrounding a second body part for receiving wave energy transmitted through a portion of said body. A second circuit means is connected to each of the plurality of receiving transducers for detecting the magnitude of the wave energy received by each.

Further objects and features of the invention will be apparent from the following specification and claims when considered in connection with the accompanying drawings illustrating the preferred embodiment of the invention.

Figure 1:
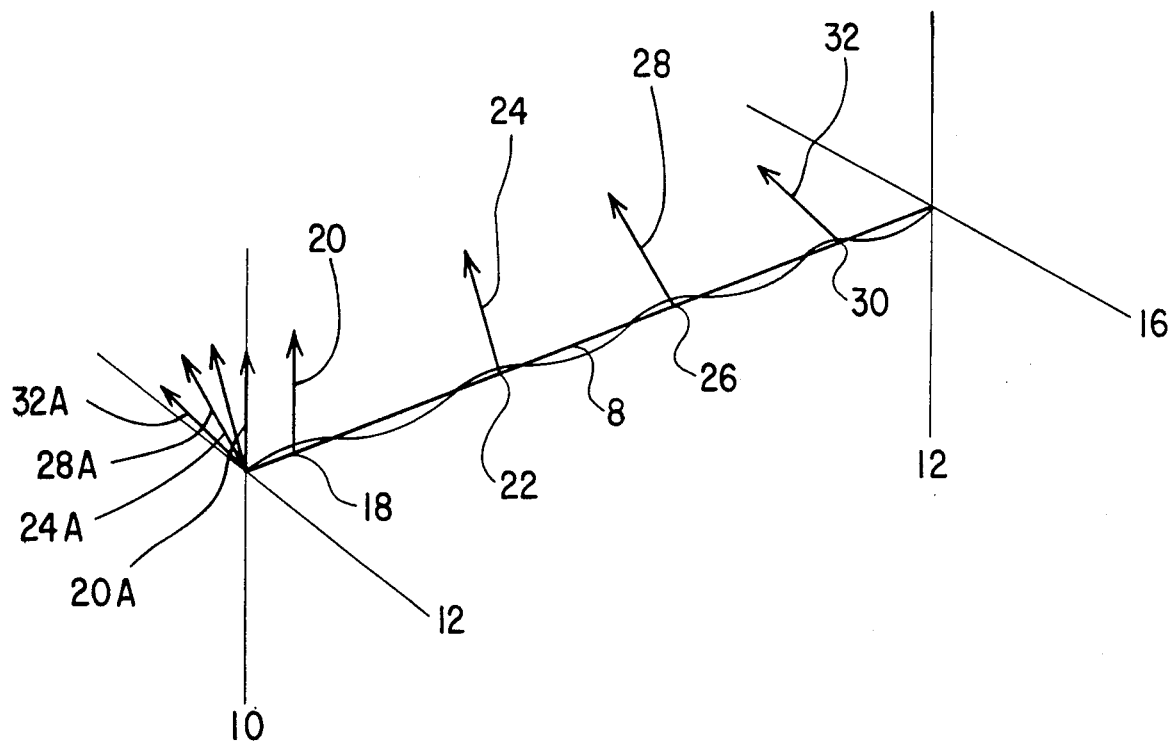
FIG. 1 is a graphical diagram illustrating the theory and operation of the preferred embodiments of the invention.

In describing the invention as illustrated in the drawings, specific terminology will be restored to for the sake of clarity. However, it is not intended to be limited to the specific terms so selected and it is to be understood that each specific term includes all technical equivalents which operate in a similar manner to accomplish a similar purpose.

DETAILED DESCRIPTION

Wave energy, such as electromagnetic or sonic waves, may be transmitted through various media. If the transmission medium is a physical body then wave energy may be applied at one part of the body, transmitted through the body and received at another body part. Changes in the wave energy effected by the portion of the body through which the wave energy is transmitted, may be found by comparing the input or applied wave energy to the received or detected wave energy. Wave energy has, of course, various parameters. These include amplitude, frequency, phase and polarization.

I have discovered that unique characteristics of a portion of a body may be determined by measuring the shift in polarization effected by the body portion upon wave energy transmitted through that body portion. Thus, wave energy is applied to a first part of a body with a selected polarization with respect to the body.

Then the polarization of the wave energy transmitted through the portion of the body from the first body part is detected at a second body part. The shift in polarization of the wave energy as it is transmitted from the first body part to the second body part may then be subjectively analyzed by means of the human judgement of doctors or technicians or alternatively may be machine processed in many ways including the manner described below. The preferred form of wave energy is a physical vibration or sonic signal although electromagnetic signals or combinations of electromagnetic and physical vibration sonic signals should also reveal useful information.

The polarization of wave energy is the orientation of its oscillations or in more complex systems may be the orientation of the oscillation of maximum amplitude. For example, a tightly stretched string may be driven at one point with vertical oscillations. These oscillations would ordinarily be transmitted along the string so that other points will similarly oscillate in a vertical orientation. Thus, a small segment of string selected at random will, unless it is a node, be found to physically move back and forth in a vertical plane. Ordinarily, if a string is driven in a horizontal direction or at any other orientation, the entire string will vibrate or oscillate in the plane of its driving energy.

However, more complex bodies may cause a shift in the orientation of the oscillations. Oscillations applied in a vertical direction for example, may be transmitted through the medium in such a manner that at a point spaced from the point of application, the oscillations of the medium occur at some inclination to the vertical.

FIG. 1, for example, diagrammatically and pictorially illustrates the polarization shift of an applied oscillation. Line 8 represents a body with axes 10 and 12 drawn at one end and axes 14 and 16 at another. Intersecting axes are drawn perpendicular to each other and each pair of axes is perpendicular to the body 8.

If energy is applied in a vertical direction at a point 18 and is represented by vertical vector 20, this energy will be transmitted along the body 8. The applied vector 20 may be reflected onto the axes 10 and 12 as vector 20A At a point 22 spaced from point 18 the oscillations may be oriented in the direction illustrated by vector 24, which is reflected as vector 24A. Similarly, at a more further spaced point 26, the oscillation may be represented by a further rotated vector 28 reflected as vector 28A. Finally, the wave energy may be received at a point 30 at which the oscillations are further rotated to the orientation of vector 32 reflected as vector 32A onto axes 10 and 12.

Figure 2:
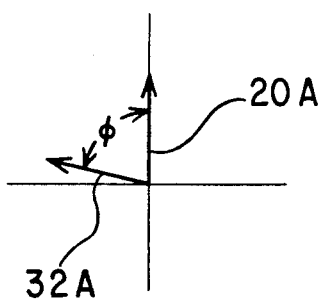
FIG. 2 is a graph further illustrating the theory and operation of the preferred embodiment of the invention.

Reflected vectors 20A and 32A are illustrated in FIG. 2. The difference in orientation between these two vectors is the polarization shift $\phi$ and is dependent upon the characteristics of the medium as well as the distance from the application point 18 to the detection point 30.

In most physical bodies some oscillating wave energy will be observed in all directions at a place spaced from the place of application of the wave energy. This could be represented by a graph 34 illustrated in FIG. 3 which is the continuum of points for all vectors representing detected oscillations in all directions. The shape and magnitude of such a pattern 34 is indicative of the characteristics of the medium through which the wave energy was transmitted. However, since such a pattern normally exhibits peaks, the peak may be represented for some purposes by a peak vector 36. Data representing either the pattern 34 or the vector 36 may be stored and processed in computing machines, for example, in the form of rectangular or radial coordinates.

Figure 4:
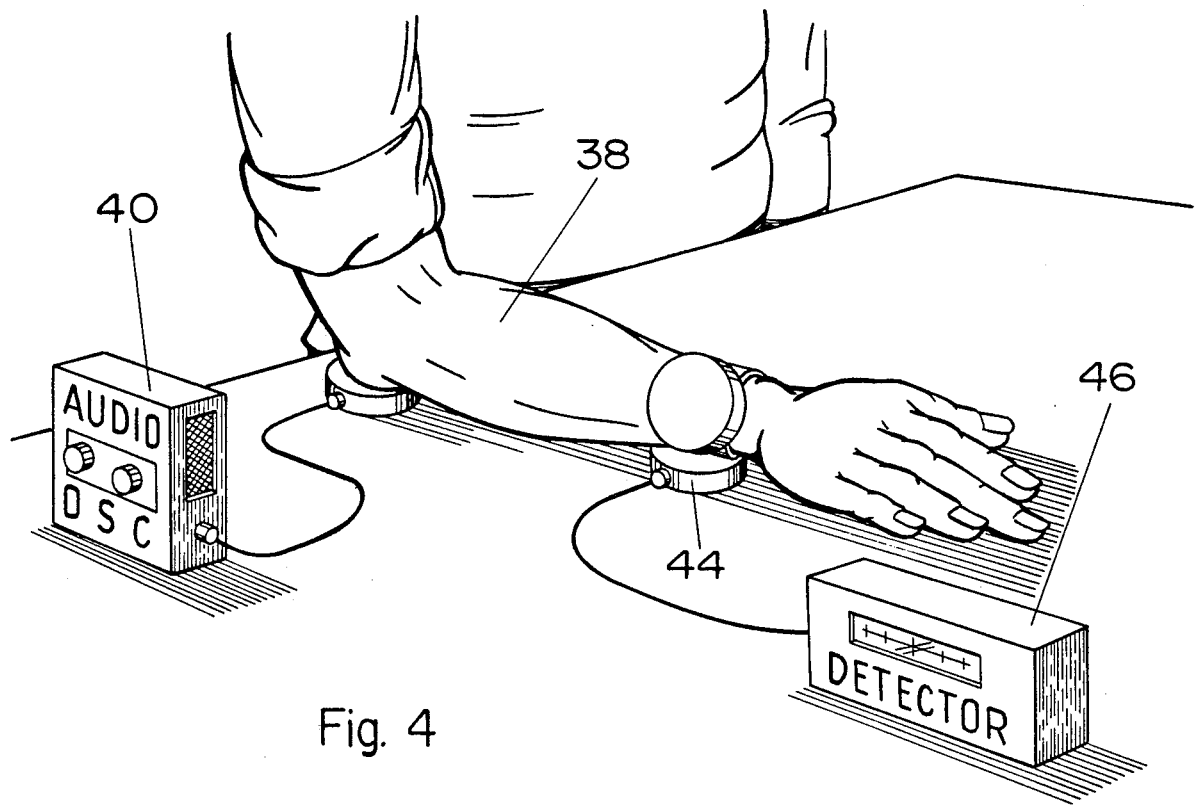
FIG. 4 is a diagrammatic pictorial view illustrating a rudimentary form of the present invention.

FIG. 4 represents a simple embodiment of the invention used to analyze the characteristics of a human arm 38. An electronic audio oscillator 40, preferably having a variable frequency, is connected to energize a transducer 42. Typically the transducer would be of the piezoelectric or electromagnetic type. of course, low energy, high frequency electromagnetic radiation systems might alternatively be used.

The transducer 42 applies an oscillatory wave energy signal to a first part of the body such as to the bony protrusion of the ulna bone at a selected polarization with respect to the body part. For example, if the transducer is positioned directly beneath the bony protrusion and a conventional transducer such as an audio speaker is used, the oscillations will be applied at a vertical polarization. A second transducer 44, which may be of the same type as transducer 42, for converting the transmitted vibrations to electrical signals is positioned in a vicinity of the wrist. It is connected to an electronic amplitude detector 46 to provide an output which is proportional to the amplitude of the signal transmitted to the receiving transducer 44. Such an output could, for example, be a digital read-out meter.

An operator can then position the transducer 44 at various angular positions about the wrist until the position of maximum amplitude is found. The orientation of this position of maximum amplitude is then noted so that the difference between it and the vertical orientation of the applied signal may then be determined.

Figure 3:
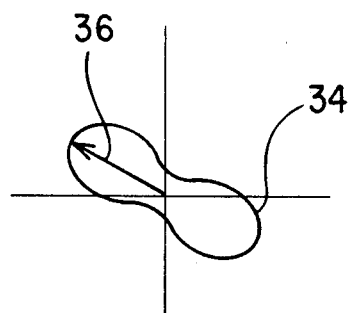
FIG. 3 is a graph further illustrating an aspect of the theory and operation of an embodiment of the invention.

Alternatively, the amplitude of the oscillations at a plurality of spaced positions can be recorded and utilized to manually plot the pattern such as pattern 34 illustrated in FIG. 3.

The same procedure can subsequently be applied to a subsequent arm. Recorded data representing the polarization shift or pattern can be compared to previously recorded similar data to determine whether the polarization shift of the first test is sufficiently close to the subsequently recorded data that it represents the arm of the identically same person.

Similarly, medical personnel can record data for body parts suffering from differing types of known trauma or disease. Subsequent patients can be diagnosed according to the invention and the recorded data of the patient compared to data representing known medical conditions. A similarity in characteristics can then be utilized to aid a doctor in the diagnosis of similar conditions.

Of course, the apparatus illustrated in FIG. 4 is in a most elementary, crude and unsophisticated form. More sophisticated automatic apparatus will become apparent from the disclosure of this patent application to those skilled in the electronics and computing arts.

Figure 5:
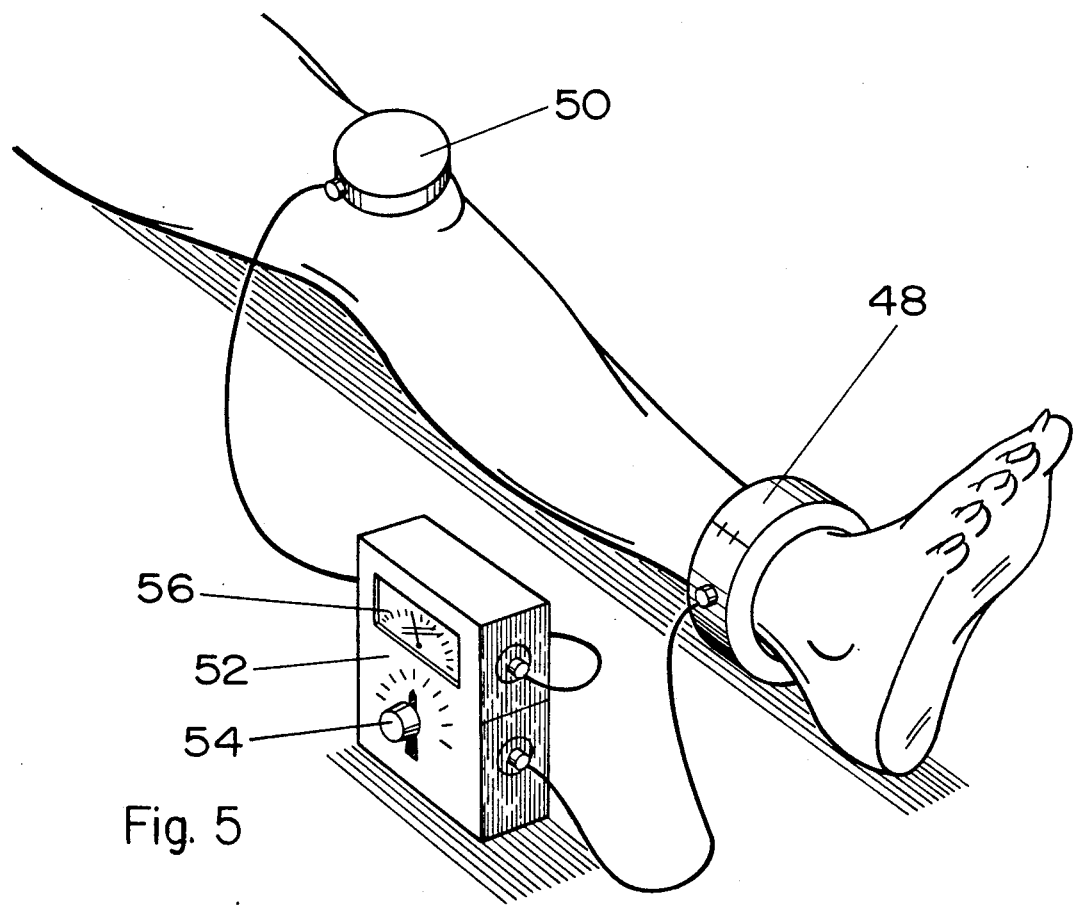
FIG. 5 is a diagrammatic pictorial view illustrating an alternative embodiment of the invention.

The apparatus of FIG. 4 can be improved in the manner illustrated in FIG. 5 by providing a plurality of receiving transducers 48 which are mounted in side-by-side arcuate arrangement and at least partially surrounding the second part of the body. Oscillating wave energy is applied by a transducer 50 connected to an audio oscillator in the cabinet 52. In a most rudimentary form, each of the transducers in the receiving transducer 48 may be connected to a rotary switch 54 so that each may be selectively connected to the input of a detector and display meter 56 built into the cabinet 52.

In its operation, each of the transducers would detect the oscillations at a different angular orientation. The signals from each transducer may be observed on the meter 56 by selecting the particular transducer with the rotary switch 54. Automatic circuitry including analog to digital convertors, sequencing and switching circuits and other computing circuits can be used to automatically perform the same operations and electronically record the same data.

Furthermore, it will be apparent to those skilled in the art that computer techniques can be utilized to graphically display a pattern such as that illustrated in FIG. 3 or alternatively to also compute the polarization shift by the subtraction of the initial polarization from the detected polarization. The machine would also easily be designed for selecting the particular transducer and therefore the polarization orientation angle of the maximum amplitude of oscillation.

Further, once data representing the polarization shift is computed it would be elementary to store such data in the computer storage for processing at a subsequent time. For example, elementary computer technology can be applied to compare a subsequently measured polarization shift to an earlier measured polarization shift to determine whether the two are within a preselected tolerance. A computer could then signal an indication that the subsequently measured person is identical to the earlier measured person if the polarization shifts are within the preselected tolerance.

The method of the invention may be further enhanced by utilizing wave energy signals at a plurality of different frequencies. For example, a polarization shift characteristic can be obtained by plotting or recording polarization shift against frequency. Such a plot would give a polarization shift characteristic for a particular body. Subsequently, similar data could be obtained and plotted or recorded for a subsequent body. Comparison of these data may then be used for identification of individuals by determining whether the characteristics are within a preselected tolerance or for medical diagnosis by comparing one polarization shift characteristic with a known polarization shift characteristic for a particular condition.

Figure 6:
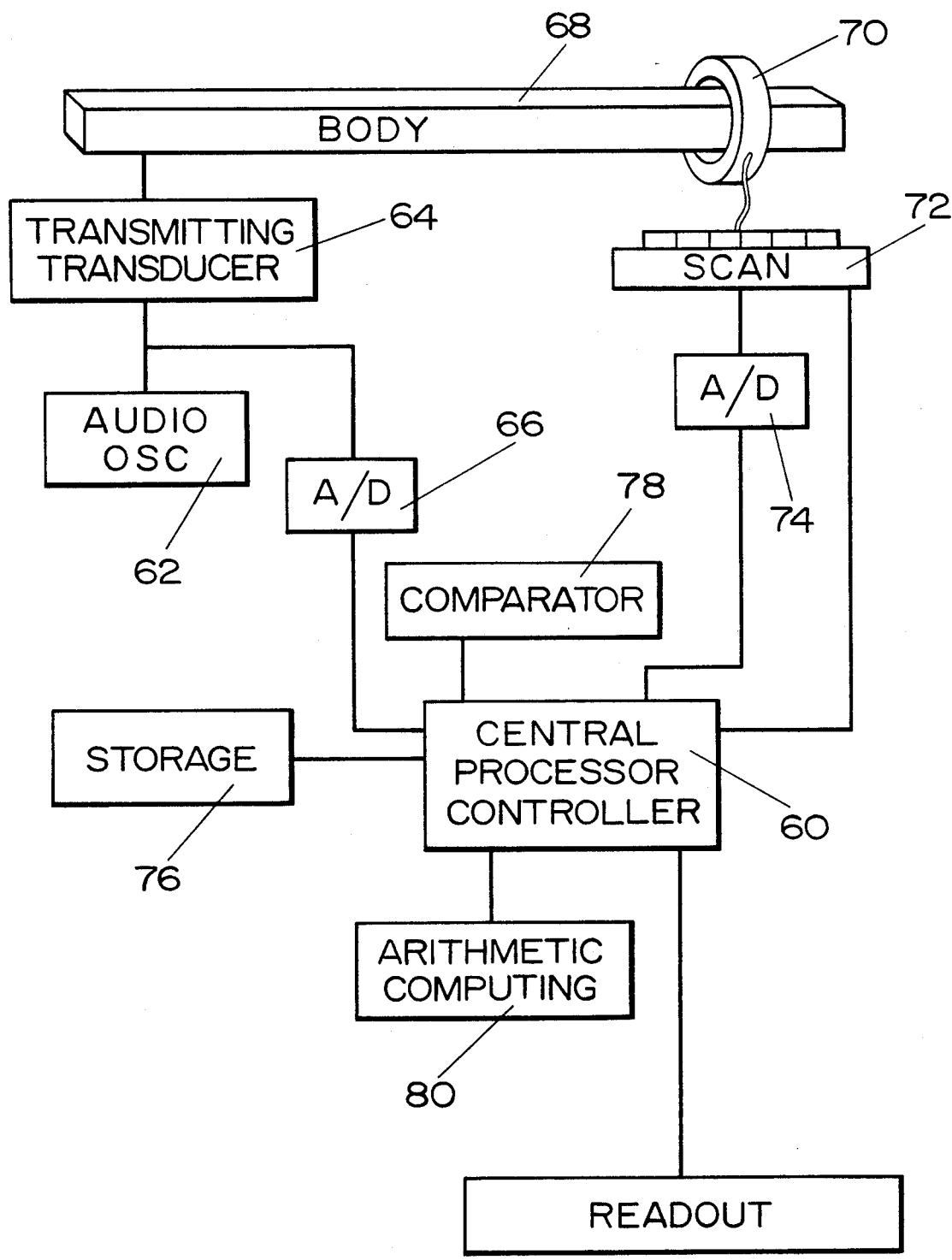
FIG. 6 is a block diagram illustrating a more sophisticated embodiment of the present invention.

FIG. 6 is a block diagram utilizing modern data processing equipment as an aid in performing the method of the present invention. The heart of the processing system is a central processorcontroller 60. An audio oscillator 62 drives the transmitting transducer 64 and also applies oscillator frequency data to the central processor through an analog/digital converter 66. The transducer 64 applies oscillating wave energy to the body 68 which is transmitted along the body 68 to a receiving transducer 70 of the type illustrated in FIG. 5. Each of the outputs from the transducer 70 is connected to a register 72 for scanning each of the individual component transducers in sequence upon the command of the central processor 60. Data representing the amplitude of the received wave energy for each polarization angle is applied to the central processor through an analog to digital converter 74 and stored in the storage means 76.

The receiving transducer 70 would have an indicia thereon so that a particular one of its component transducers would represent no polarization shift and this particular one will be properly oriented with respect to the transmitting transducer 64. Data gathered and stored during the measurement of one body and data from a subsequent body can be processed by the central processor with the aid of comparator 78 and arithmetic, data computing circuits.

It is to be understood that while the detailed drawings and specific examples given describe the preferred embodiments of the invention, they are the for purpose of illustration only, that the apparatus of the invention as well as the method is not limited to the precise details and conditions disclosed and that various changes may be made therein without departing from the spirit of the invention which is defined by the following claims.

What is claimed is:
1. A method for determining a body portion characteristic, the method comprising measuring the polarization shift effected by said body portion upon wave energy transmitted though said body portion.
2. A method for detecting a body portion characteristic, the method comprising:
   a. applying wave energy to a first part of a body with a selected polarization with respect to said body;
   b. detecting the polarization at a second part of said body of the wave energy transmitted through a portion of said body from said first body part.
3. A method according to claim 2 wherein said wave energy is a physical vibration, sonic signal.
4. A method according to claim 2 wherein said wave energy is an electromagnetic signal.
5. A method according to claim 2 wherein said wave energy comprises both electromagnetic and physical vibration sonic signals.
6. A method for use in the analysis of a body portion, the method comprising:
   a. applying an oscillatory wave energy signal to a first part of a first body with a selected polarization with respect to said body part;
   b. detecting the polarization at a second part of said first body of the signal transmitted through a portion of said body;
   c. computing and storing data representing the polarization shift of said signal;
   d. subsequently applying an oscillatory signal to the first part of a subsequent body corresponding to the first part of said first body with a selected polarization with respect to said subsequent body part;
   e. detecting the polarization at the second part of said subsequent body, which corrresponds to the second part of said first body, of the signal transmitted through a portion of said subsequent body;
   f. computing data representing the polarization shift of said subsequently applied signal.
7. A method according to claim 6 wherein the method further comprises the step of displaying the data representing each of said polarization shifts for aiding subjective human comparison.
8. A method according to claim 6 wherein the method further comprises the steps of computing and displaying the difference between said polarization shifts.
9. A method according to claim 6 for use as an aid in identifying individual persons, said method further comprising the steps of comparing the difference between said polarization shifts and preselected tolerance to determine whether said difference is less than said tolerance.
10. A method according to claim 6 wherein said signal comprises a plurality of signal frequencies.
11. A method according to claim 10 wherein the difference in polarization shift for each frequency is computed and displayed.

* * * * *

UNITED STATES PATENT OFFICE
CERTIFICATE OF CORRECTION

Patent No. 3,990,436         Dated November 9, 1976

Inventor(s) James H. Ott

It is certified that error appears in the above-identified patent and that said Letters Patent are hereby corrected as shown below:

Figure 4 of the drawings should appear as shown.

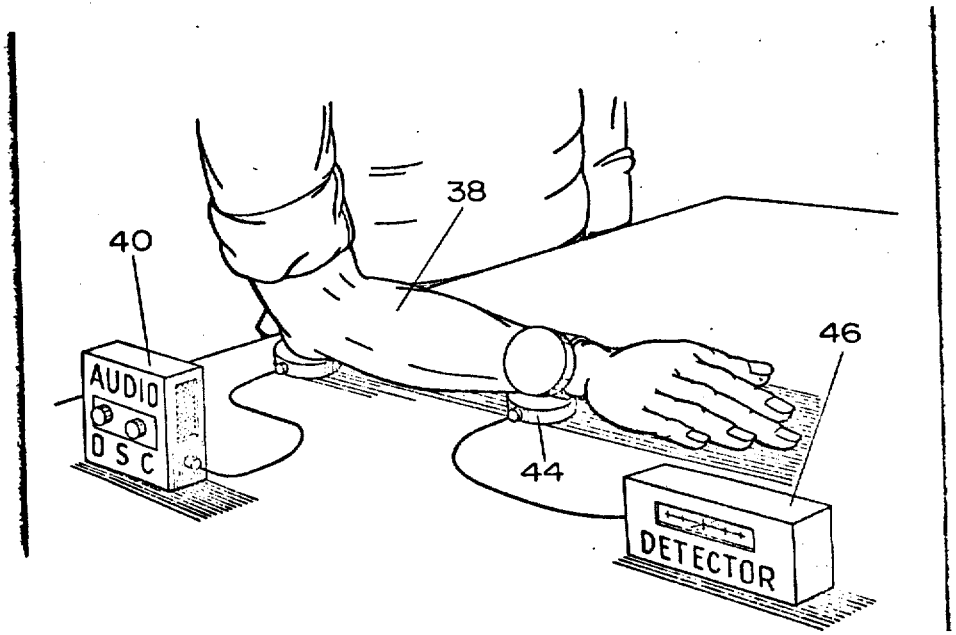

Signed and Sealed this

Fourth Day of January 1977

[SEAL]

Attest:

RUTH C. MASON
*Attesting Officer*

C. MARSHALL DANN
*Commissioner of Patents and Trademarks*